United States Patent [19]

Bundy

[11] 4,001,286

[45] Jan. 4, 1977

[54] PHENYL-SUBSTITUTED PROSTAGLANDIN-β-TYPE ANOLOGS

[75] Inventor: Gordon L. Bundy, Portage, Mich.

[73] Assignee: The Upjohn Company, Kalamazoo, Mich.

[22] Filed: Dec. 29, 1975

[21] Appl. No.: 645,277

Related U.S. Application Data

[60] Division of Ser. No. 431,011, Jan. 7, 1974, Pat. No. 3,987,087, which is a continuation-in-part of Ser. No. 167,446, July 29, 1971, abandoned, which is a continuation-in-part of Ser. No. 86,303, Nov. 2, 1970, abandoned.

[52] U.S. Cl. .................. 260/410.9 R; 424/305; 424/308; 260/240 R; 260/340.9; 260/343.6; 260/408; 260/410; 260/410.5; 260/413; 260/456 R; 260/468 D; 260/475 A; 260/520 B; 260/586 R

[51] Int. Cl.² .................. C07C 5/22; C07C 69/76

[58] Field of Search ........ 260/410.9, 473 A, 520 B, 260/410, 410.5, 408, 413

[56]         References Cited

FOREIGN PATENTS OR APPLICATIONS 2,154,309   4/1972   Germany .................. 260/473 A

*Primary Examiner*—Paul J. Killos
*Attorney, Agent, or Firm*—Morris L. Nielsen

[57]         ABSTRACT

This invention is a group of phenyl-substituted PGE-type, PGF-type, PGA-type and PGB-type compounds, and processes for making them. These compounds are useful for a variety of pharmacological purposes, including anti-ulcer, inhibition of platelet aggregation, increase of nasal patency, labor inducement at term, and wound healing.

91 Claims, No Drawings

PHENYL-SUBSTITUTED PROSTAGLANDIN-β-TYPE ANOLOGS

CROSS REFERENCE TO RELATED APPLICATIONS

This is a division of application Ser. No. 431,011, filed Jan. 7, 1974 which in turn is a continuation-in-part of my copending application Ser. No. 167,446, filed July 29, 1971 now abandoned, which in turn is a continuation-in-part of my application Ser. No. 86,303, filed Nov. 2, 1970, now abandoned.

DESCRIPTION OF THE INVENTION

This invention relates to compositions of matter, and to methods and intermediates for producing them. The several aspects of this invention relate to novel analogs of some of the known prostaglandins, for example, prostaglandin $E_1$ ($PGE_1$, prostaglandin $E_2$ ($PGE_2$), prostaglandin $F_1$ ($PGF_{1\alpha}$ and $PGF_{1\beta}$), prostaglandin $F_2$ ($PGF_{2\alpha}$ and $PGF_{2\beta}$), prostaglandin $A_1$ $PGA_1$), prostaglandin $A_2$ ($PGA_2$), prostaglandin $B_1$ ($PGB_1$), prostaglandin $B_2$ ($PGB_2$), and the dihydro derivatives of $PGE_1$, $PGF_{1\alpha}$, $PGF_{1\beta}$, $PGA_1$, and $PGB_1$, to novel methods for producing those novel prostaglandin analogs, and to novel chemical intermediates useful in those novel methods. In particular, the novel prostaglandin analogs of this invention are phenyl-substituted in the C-13 to C-20 chain.

The essential material for this application, including the background of the invention, the disclosure of the invention, and the description of the preferred embodiments, including Preparations and Examples, is incorporated by reference from pending and commonly owned U.S. Pat. application Ser. No. 431,011, filed Jan. 7, 1974, now U.S. Pat. No. 3,987,087 under the provisions of M.P.E.P. 608.01(p).

SUMMARY OF THE INVENTION

It is the purpose of this invention to provide novel prostaglandin analogs, and processes for making them.

The novel prostaglandin analogs of this invention each have a benzene ring as part of the C-13 to C-20 chain of the prostanoic acid structure (I) acid of 8-isoprostanoic acid structure (VII). That benzene ring is present as a substituted or unsubstituted phenyl moiety (1) attached as a substituent replacing one of the hydrogens on one of the methylenes between C-15 and the terminal methyl of the prostanoic acid or 8-isoprostanoic acid structure or (2) attached to the terminal or omega carbon of the C-16 to C-20 portion of the chain, replacing either (a) one of the hydrogens of the terminal methyl, (b) the entire terminal methyl, or (c) the terminal methyl plus one to four of the methylenes adjacent to that terminal methyl. Formulas IX and X, trinor and dinor indicate absence of the terminal —CH$_2$—CH$_2$—CH$_3$ and the terminal —CH$_2$—CH$_3$, respectively, of $PGE_1$ and $PGF_{2\alpha}$. The words nor, dinor, trinor, tetranor, and pentanor in the names given here and hereinafter for novel prostaglandins of this invention are to be construed as indicating the number of carbon atoms, i.e. one, 2, 3, 4 or 5, missing from the C-16 to C-20 position of the prostanoic acid carbon skeleton. The phenyl or substituted phenyl moiety is attached to the remaining portion of the prostanoic acid skeleton, i.e., to C-19 for the nor-compounds, to C-18 for the dinor compounds, to C-17 for the trinor compounds, to C-16 for the tetranor compounds, and to C-15 for the pentanor compounds. In addition, the term can include carbon atoms missing from the C-1 to C-7 position of the prostanoic acid skeleton, for example, 17-phenyl-2,18,19,20-tetranor $PGF_{2\alpha}$.

Some of the novel prostaglandin analogs of this invention differ structurally in other ways from the known prostanoic acid derivatives, having, for example, more or fewer carbon atoms in the C-1 to C-7 chain of prostanoic acid, and having one or more alkyl and/or fluoro substituents in that chain or in the C-13 to C-20 chain of prostanoic acid.

Each of the novel phenyl-substituted prostaglandin analogs of this invention is encompassed by one of the following formulas or by the combination of that formula and its mirror image:

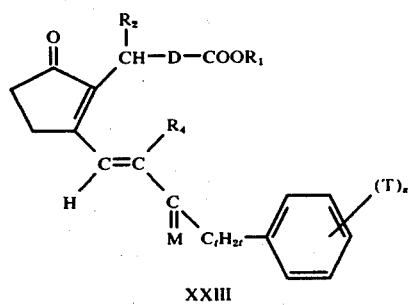

XXIII

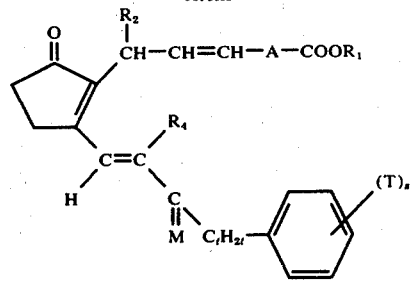

XXIV

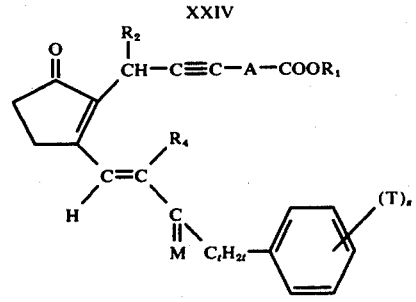

XXV

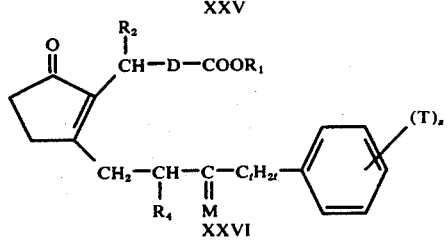

XXVI

Formulas XI to XIV represent phenyl-substituted compounds of the PGE type. Formulas XV to XVIII represent phenyl-substituted compounds of the PGF type. Formulas XIX to XXII represent phenyl-substituted compounds of the PGA type. Formulas XXIII to XXVI represent phenyl-substituted compounds of the PGB type.

In Formulas XXIII to XXVI, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2 to 3 chloro or alkyl of one to 4 carbon atoms, inclusive, or ethyl substituted in the β-position with 3 chloro, 2 or 3 bromo, or 1, 2, or 3 iodo. M is

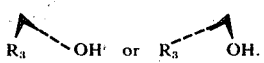

$R_2$, $R_3$, and $R_4$ are hydrogen or alkyl of one to 4 carbon atoms, inclusive. The moiety -$C_tH_{2t}$- represents (a) a valence bond or (b) alkylene of one to 10 carbon atoms, inclusive, substituted with zero, one, or 2 fluoro, with one to 7 carbon atoms, inclusive, between

and the ring. When one or 2 fluoro are present as substituents of —$C_tH_{2t}$, that moiety will contain 2t-1 or 2t-2 hydrogen atoms, respectively, rather than 2t hydrogen atoms. The symbol T represents alkyl of one to 4 carbon atoms, inclusive, fluoro, chloro, trifluoromethyl, or —$OR_9$, wherein $R_9$ is hydrogen or alkyl of one to 4 carbon atoms, inclusive. The symbol s represents zero, one, 2, or 3. Regarding the combination $(T)_s$ attached to the phenyl ring, no more than two T's are other than alkyl. Except for that proviso, when two or three T's are present as substituents, they are the same or different. The symbol D represents alkylene of 3 to 12 carbon atoms, inclusive, substituted with zero, one, 2, 3, or 4 fluoro, with 3 to 7 carbon atoms, inclusive, between —$CHR_2$— and $COOR_1$, and with the proviso that when 3 or 4 fluoro are present, they are all substituents of the carbon atoms alpha and beta to $COOR_1$. The symbol A represents alkylene of one to 10 carbon atoms, inclusive, substituted with zero, one, 2, 3, or 4 fluoro, with one to 5 carbon atoms, inclusive, between =CH- or  C- and —$COOR_1$, and with the proviso that when 3 or 4 fluoro are present, they are all substituents of the carbon atoms alpha and beta to —$COOR_1$.

Formulas XXIII to XXVI include the separate isomers wherein M is either

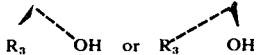

i.e. where the side chain hydroxy is in either S (alpha) or R (epi or beta) configuration. Referring to the prostanoic acid atom numbering (formula I above), the point of attachment corresponds to C-15, and, herein regardless of the variation in the C-1 to C-7 carbon chain, these epimers are referred to as C-15 epimers.

Included in Formula XXIV are both the cis and the trans compounds with respect to the C-5 to C-6 carbon-carbon double bond in the carboxyl-terminated side chain. In all of the compounds containing the C-13 to C-14 double bond, that carbon-carbon double bond is in trans configuration, and the chain containing $R_4$ is attached to the cyclopentane ring in beta configuration in compounds encompassed by Formulas XI to XXII.

Formulas XXIII to XXVI include lower alkanoates, and also pharmacologically acceptable salts when $R_1$ is hydrogen.

Like the natural prostaglandins described above, these novel phenyl-substituted prostaglandin compounds have several centers of asymmetry. The novel compounds of this invention include (a) compounds having the same configuration as naturally occurring prostaglandins and (b) racemic compounds of (a) plus optically active enantiomeric forms thereof. As discussed hereinabove, two structural formulas are required to define accurately these racemic compounds. Formulas XXIII through XXVI, inclusive, are intended to represent optically active prostanoic acid analogs having the same absolute configuration as the naturally-occurring prostaglandins. However, for convenience in the charts herein only a single formula is used to define not only the optically active form but also the racemic compounds which generally undergo the same reactions.

The embodiments of the invention in which an exclusive property or privilege is claimed are defined as follows:

1. A compound of the formula

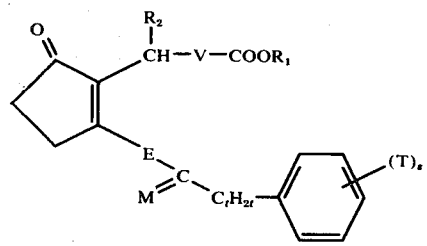

wherein E is —$CH_2$—$CHR_4$— or trans —CH=$CR_4$—; wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro; wherein M is

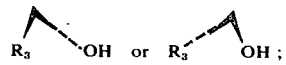

wherein $R_2$, $R_3$, and $R_4$ are hydrogen or alkyl of one to 4 carbon atoms, inclusive; wherein $C_tH_{2t}$ represents a valence bond or alkylene of one to 10 carbon atoms, inclusive, substituted with zero, one, or 2 fluoro, with one to 7 carbon atoms, inclusive, between

and the phenyl ring; wherein T is alkyl of one to 4 carbon atoms, inclusive, fluoro, chloro, trifluoromethyl, or —$OR_9$, wherein $R_9$ is hydrogen, or alkyl of one to 4 carbon atoms, inclusive, and s is zero, one, 2, or 3, with the proviso that not more than two T's are other than alkyl; and wherein V is (a) alkylene of 3 to 12 carbon atoms, inclusive, substituted with zero, one, 2, 3, or 4 fluoro, with 3 to 7 carbon atoms, inclusive, between —$CHR_2$— and $COOR_1$, with the proviso that when 3 or 4 fluoro are present, they are all substituents of the carbon atoms alpha and beta to —$COOR_1$, (b) —CH=CH—A—, cis or trans, or (c) —C≡C—A—, wherein A is alkylene of one to 10 carbon atoms, inclusive, substituted with zero, one, 2, 3, or 4 fluoro, with one to 5 carbon atoms, inclusive, between =CH— (or ≡ C—) and —COOR₁, with the proviso that when 3 or 4 fluoro are present, they are all substituents of the carbon atoms alpha and beta to —COOR₁, with the further proviso that when E is —CH₂—CHR₄— V is (a) above; including the lower alkanoates thereof, and the pharmacologically acceptable salts thereof when R₁ is hydrogen.

2. A compound according to claim 1 wherein V is (a) —(CH₂)ₐ—X—, (b) —CH=CH—(CH₂)ᵦ—X—, or (c) —C ≡ C—(CH₂)ᵦ—X—, wherein a is one, 2, 3, 4, or 5, b is zero, one, 2, or 3, and X is ethylene substituted by one, 2, 3, or 4 fluoro, methyl, or ethyl, or by one alkyl of 3 or 4 carbon atoms.

3. A compound according to claim 2 wherein a is 3 and b is one.

4. 2,2-Difluoro-17-phenyl-18,19,20-trinor-PGB₂, methyl ester, a compound according to claim 3.

5. 15(S)-15-Methyl-2,2-difluoro-17-phenyl-18,19,20-trinor-PGB₂, methyl ester, a compound according to claim 3.

6. A compound according to claim 1 wherein V is (a) alkylene of 3 to 12 carbon atoms, inclusive, substituted with zero, one, 2, 3, or 4 fluoro, with 5 carbon atoms in the chain between —CHR₂— and —COOR₁, (b) —CH=CH—A—, cis or trans, or (c) —C ≡ C—A—, wherein A is alkylene of one to 10 carbon atoms, inclusive, substituted with zero, one, 2, 3, or 4 fluoro, with 3 carbon atoms in the chain between =CH— (or ≡ C—) and —COOR₁.

7. A compound according to claim 6 wherein $C_tH_{2t}$ is limited to one to 4 carbon atoms in the chain between

and the phenyl ring.

8. A compound according to claim 7 wherein V is alkylene of 3 to 12 carbon atoms, inclusive, substituted with zero, one, 2, 3, or 4 fluoro, with 5 carbon atoms in the chain between —CHR₂— and —COOR₁; and wherein E is trans—CH=CH—.

9. A compound according to claim 8 wherein M is

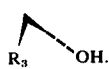

10. A compound according to claim 9 wherein R₃ is hydrogen.

11. A compound according to claim 10 wherein $C_tH_{2t}$ is ethylene.

12. A compound according to claim 11 wherein R₁ is hydrogen, and the pharmacologically acceptable salts thereof.

13. 17-Phenyl-18,19,20-trinor-PGB₁, a compound according to claim 12.

14. A compound according to claim 11 wherein R₁ is alkyl of one to 8 carbon atoms, inclusive.

15. 17-Phenyl-18,19,20-trinor-PGB₁, methyl ester, a compound according to claim 14.

16. A compound according to claim 10 wherein $C_tH_{2t}$ is

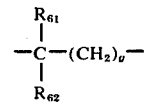

wherein g is zero, one, 2, or 3, and wherein R₆₁ and R₆₂ are hydrogen, alkyl of one to 4 carbon atoms, inclusive, or fluoro, being the same or different, with the proviso that R₆₂ is fluoro only when R₆₁ is hydrogen or fluoro, and with the further proviso that R₆₁ and R₆₂ are not both hydrogen.

17. A compound according to claim 16 wherein R₆₁ and R₆₂ are alkyl of one to 4 carbon atoms, inclusive.

18. A compound according to claim 17 wherein $C_tH_{2t}$ is —C(CH₃)₂—CH₂—.

19. A compound according to claim 18 wherein R₁ is hydrogen, and the pharmacologically acceptable salts thereof.

20. 16,16-Dimethyl-17-phenyl-18,19,20-trinor-PGB₁, a compound according to claim 19.

21. A compound according to claim 18 wherein R₁ is alkyl of one to 8 carbon atoms, inclusive.

22. 16,16-Dimethyl-17-phenyl-18,19,20-trinor-PGB₁, methyl ester, a compound according to claim 21.

23. A compound according to claim 10 wherein $C_tH_{2t}$ is trimethylene.

24. A compound according to claim 23 wherein R₁ is hydrogen, and the pharmacologically acceptable salts thereof.

25. 18-Phenyl-19,20-dinor-PGB₁, a compound according to claim 24.

26. A compound according to claim 23 wherein R₁ is alkyl of one to 8 carbon atoms, inclusive.

27. 18-Phenyl-19,20-dinor-PGB₁, methyl ester, a compound according to claim 26.

28. A compound according to claim 9 wherein R₃ is methyl.

29. A compound according to claim 28 wherein $C_tH_{2t}$ is ethylene.

30. A compound according to claim 29 wherein R₁ is hydrogen; and the pharmacologically acceptable salts thereof.

31. 15(S)-15-Methyl-17-phenyl-18,19,20-trinor-PGB₁, a compound according to claim 30.

32. A compound according to claim 29 wherein R₁ is alkyl of one to 8 carbon atoms, inclusive.

33. 15(S)-15-Methyl-17-phenyl-18.19,20-trinor-PGB₁, methyl ester, a compound according to claim 32.

34. A compound according to claim 28 wherein $C_tH_{2t}$ is trimethylene.

35. A compound according to claim 34 wherein R₁ is hydrogen, and the pharmacologically acceptable salts thereof.

36. 15(S)-15-Methyl-18-phenyl-19,20-dinor-PGB₁, a compound according to claim 35.

37. A compound according to claim 34 wherein R₁ is alkyl of one to 8 carbon atoms, inclusive.

38. 15(S)-15-Methyl-18-phenyl-19,20-dinor-PGB₁, a compound according to claim 37.

39. A compound according to claim 8 wherein M is

40. A compound according to claim 39 wherein $R_3$ is hydrogen.

41. A compound according to claim 39 wherein $R_3$ is methyl.

42. A compound according to claim 41 wherein $C_tH_{2t}$ is ethylene.

43. A compound according to claim 42 wherein $R_1$ is hydrogen, and the pharmacologically acceptable salts thereof.

44. 15(R)-15-Methyl-17-phenyl-18,19,20-trinor-$PGB_1$, a compound according to claim 43.

45. A compound according to claim 42 wherein $R_1$ is alkyl of one to 8 carbon atoms, inclusive.

46. 15(R)-15-Methyl-17-phenyl-18,19,20-trinor-$PGB_1$, methyl ester, a compound according to claim 45.

47. A compound according to claim 7 wherein V is —CH=CH—A—, cis to trans, wherein A is alkylene of one to 10 carbon atoms, inclusive, substituted with zero, one, 2, 3, or 4 fluoro, with 3 carbon atoms in the chain between =CH— and —$COOR_1$; and wherein E is trans—CH=CH—.

48. A compound according to claim 47 wherein M is

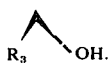

49. A compound according to claim 48 wherein $R_3$ is hydrogen.

50. A compound according to claim 49 wherein $C_tH_{2t}$ is ethylene.

51. A compound according to claim 50 wherein $R_1$ is hydrogen, and the pharmacologically acceptable salts thereof.

52. 17-Phenyl-18,19,20-trinor-$PGB_2$, a compound according to claim 51.

53. 17-(p-Chlorophenyl)-18,19,20-trinor-$PGB_2$, a compound according to claim 51.

54. 17-(p-Fluorophenyl)-18,19,20-trinor-$PGB_2$, a compound according to claim 51.

55. A compound according to claim 50 wherein $R_1$ is alkyl of one to 8 carbon atoms, inclusive.

56. 17-Phenyl-18,19,20-trinor-$PGB_2$, methyl ester, a compound according to claim 55.

57. 17(p-Chlorophenyl)-18,19,20-trinor-$PGB_2$, methyl ester, a compound according to claim 55.

58. 17-(p-Chlorophenyl)-18,19,20-trinor-$PGB_2$, ethyl ester, a compound according to claim 55.

59. A compound according to claim 49 wherein $C_tH_{2t}$ is

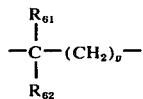

wherein g is zero, one, 2, or 3, and wherein $R_{61}$ and $R_{62}$ are hydrogen, alkyl of one to 4 carbon atoma, inclusive, or fluoro, being the same of different, with the proviso that $R_{62}$ is fluoro only when $R_{61}$ is hydrogen or fluoro, and with the further proviso that $T_{61}$ and $R_{62}$ are not both hydrogen.

60. A compound according to claim 59 wherein R61 and $R_{62}$ are alkyl of one to 4 carbon atoms, inclusive.

61. A compound according to claim 60 wherein $C_tH_{2t}$ is —$C(CH_3)_2$—$CH_2$—.

62. A compound according to claim 61 wherein $R_1$ is hydrogen, and the pharmacologically acceptable salts thereof.

63. 16,16-Dimethyl-17-phenyl-18,19,20-trinor-$PGB_2$, a compound according to claim 62.

64. A compound according to claim 61 wherein $R_1$ is alkyl of one to 8 carbon atoms, inclusive.

65. 16,16-Dimethyl-17-phenyl-18,19,20-trinor-$PGB_2$, methyl ester, a compound according to claim 64.

66. A compound according to claim 49 wherein $C_tH_{2t}$ is trimethylene.

67. A compound according to claim 66 wherein $R_1$ is hydrogen, and the pharmacologically acceptable salts thereof.

68. 18-Phenyl-19,20-dinor-$PGB_2$, a compound according to claim 67.

69. A compound according to claim 66 wherein $R_1$ is alkyl of one to 8 carbon atoms, inclusive.

70. 18-Phenyl-19,20-dinor-$PGB_2$, methyl ester, a compound according to claim 69.

71. A compound according to claim 48 wherein $R_3$ is methyl.

72. A compound according to claim 71 wherein $C_tH_{2t}$ is ethylene.

73. A compound according to claim 72 wherein $R_1$ is hydrogen, and the pharmacologically acceptable salts thereof.

74. 15(S)-15-Methyl-17-phenyl-18,19,20-trinor-$PGB_2$, a compound according to claim 73.

75. A compound according to claim 72 wherein $R_1$ is alkyl of one to 8 carbon atoms, inclusive.

76. 15(S)-15-Methyl-17-phenyl-18,19,20-trinor-$PGB_2$, methyl ester, a compound according to claim 75.

77. A compound according to claim 71 wherein $C_tH_{2t}$ is trimethylene.

78. A compound according to claim 77 wherein $R_1$ is hydrogen, and the pharmacologically acceptable salts thereof.

79. 15(S)-15-Methyl-18-phenyl-19,20-dinor-$PGB_2$, a compound according to claim 78.

80. A compound according to claim 77 wherein $R_1$ is alkyl of one to 8 carbon atoms, inclusive.

81. 15(S)-15-Methyl-18-phenyl-19,20-dinor-$PGB_2$, methyl ester, a compound according to claim 80.

82. A compound according to claim 47 wherein M is

83. A compound according to claim 82 wherein $R_3$ is hydrogen.

84. A compound according to claim 82 wherein $R_3$ is methyl.

85. A compound according to claim 84 wherein $C_tH_{2t}$ is ethylene.

86. A compound according to claim 85 wherein $R_1$ is hydrogen, and the pharmacologically acceptable salts thereof.

87. 15(R)-15-Methyl-17-phenyl-18,19,20-trinor-$PGB_2$, a compound according to claim 86.

88. A compound according to claim 85 wherein $R_1$ is alkyl of one to 8 carbon atoms, inclusive.

89. 15(R)-15-Methyl-17-phenyl-18,19,20-trinor-$PGB_2$, methyl ester, a compound according to claim 88.

90. A compound according to claim 7 wherein v is —C≡C—A—, wherein A is alkylene of one to 10 carbon atoms, inclusive, substituted with zero, one, 2, 3, or 4 fluoro, with 3 carbon atoms in the chain between =C- and -COOR$_1$; and wherein E is trans —CH=CH—.

91. A compound according to claim 7 wherein V is alkylene of 3 to 12 carbon atoms, inclusive, substituted with zero, one, 2, 3, or 4 fluoro, with 5 carbon atoms in the chain between —CHR$_2$— and —COOR$_1$; and wherein E is —CH$_2$CH$_2$—.

* * * * *